United States Patent
Guederian

(10) Patent No.: US 7,641,695 B2
(45) Date of Patent: Jan. 5, 2010

(54) MODULAR SYSTEM FOR REPLACEMENT OF RADIAL HEAD

(75) Inventor: Gregory Guederian, Naples, FL (US)

(73) Assignee: Arthrex, Inc., Naples, FL (US)

( * ) Notice: Subject to any disclaimer, the term of this patent is extended or adjusted under 35 U.S.C. 154(b) by 238 days.

(21) Appl. No.: 11/219,744

(22) Filed: Sep. 7, 2005

(65) Prior Publication Data

US 2006/0064173 A1    Mar. 23, 2006

Related U.S. Application Data

(60) Provisional application No. 60/607,783, filed on Sep. 8, 2004.

(51) Int. Cl.
*A61F 2/38* (2006.01)

(52) U.S. Cl. .................. 623/20.11; 623/18.11

(58) Field of Classification Search ............. 623/20.11, 623/23.46, 20.12, 20.13, 17.14, 19.12, 20.22, 623/21.13, 21.16, 23.4; A61F 2/38
See application file for complete search history.

(56) References Cited

U.S. PATENT DOCUMENTS

| | | | |
|---|---|---|---|
| 2,696,817 A * | 12/1954 | Prevo .................. | 623/20.12 |
| 5,061,288 A | 10/1991 | Berggren et al. | |
| 5,314,486 A | 5/1994 | Zang et al. | |
| 5,879,395 A * | 3/1999 | Tornier et al. ............ | 623/20.13 |
| 6,217,616 B1 * | 4/2001 | Ogilvie .................. | 623/20.11 |
| 6,270,529 B1 * | 8/2001 | Terrill-Grisoni et al. . | 623/20.11 |
| 6,306,171 B1 * | 10/2001 | Conzemius .............. | 623/20.11 |
| 6,361,563 B2 | 3/2002 | Terrill-Grisoni et al. | |
| 2001/0037154 A1 * | 11/2001 | Martin .................. | 623/20.12 |
| 2003/0212457 A1 * | 11/2003 | Martin .................. | 623/20.11 |
| 2005/0033436 A1 * | 2/2005 | Schlapfer et al. ......... | 623/17.14 |
| 2005/0049710 A1 * | 3/2005 | O'Driscoll et al. ....... | 623/20.11 |

FOREIGN PATENT DOCUMENTS

| | | |
|---|---|---|
| DE | 44 12 721 | 10/1994 |
| EP | 0 132 284 | 1/1985 |
| FR | 1122634 | 9/1956 |
| FR | 2 605 878 | 5/1988 |
| FR | 2 787 013 | 6/2000 |
| GB | 2 007 980 | 5/1979 |

* cited by examiner

*Primary Examiner*—Corrine M McDermott
*Assistant Examiner*—Jason-Dennis Stewart
(74) *Attorney, Agent, or Firm*—Dickstein Shapiro LLP

(57) ABSTRACT

A modular endoprosthetic radial head implant includes an end cap secured to a cannulated body held to bone by a fixation element. The fixation element supports the cannulated body on a resected radial bone end, for example. The fixation element of one embodiment features a threaded stem with a spherical head. The stem fits distally into the cannulated body and extends through a hole formed by the distal end of the cannulated body. The spherical head nests inside the cannulated body. Polyaxial alignment between the cannulated body and the fixation element is locked using a jam nut tightened inside the cannulated body. An end cap fits into place proximally on the cannulated body. The end cap is formed of a joint surface material to provide a bearing surface.

12 Claims, 3 Drawing Sheets

MODULAR SYSTEM FOR REPLACEMENT OF RADIAL HEAD

This application claims the benefit of U.S. Provisional Application Ser. No. 60/607,783, filed Sep. 8, 2004.

BACKGROUND OF THE INVENTION

1. Field of the Invention

The present invention relates to endoprosthetic articular joint implants, and more specifically to methods and apparatus for replacing a radial head using a modular implant.

2. Description of the Related Art

Prosthetic devices for joint repair and replacement in humans and other skeletal beings are known. Joint function can be lost due to fracture or damaged joint surfaces, for example. Joints compromised in these ways typically have suffered injury or disease. Repair often entails endoprosthetic implants installed in place of resected bone-ends to replace the damaged joint and restore joint function.

A radial head implant system is disclosed in U.S. Pat. No. 6,361,563 to Terrill-Grisoni et al. The modular system includes a head and a stem. A complex system is used to adapt the radius of the head.

Joint-replacements are known that generally include an intramedullary stem anchoring a curved joint surface. U.S. Pat. No. 5,061,288 to Berggren et al. Berggren et al. discloses a joint implant that features a surface-replacing portion attached to the end of an axial support. Bristles extend radially from the axial support sufficient to be urged proximally upon insertion to the canal. The bristles consequently are biased against removal of the implant, thereby acting as barbs to anchor the surface-replacing portion of the implant on the end of resected bone. A joint-surface material features a dovetail groove that engages a base with a corresponding pin attached to the axial support.

French patent document no. 2,605,878 in the name of Condamine discloses a two part joint prosthesis. Referring to FIGS. 1-3 of Condamine, the implant features an articulating surface portion that is adhered to a ribbed intramedullary stem. Another French patent document, no. 1,122,634 in the name of van Steenbrugghe discloses implants with coated spherical ends. The coating can include a polymer, such as Plexiglas, Lucite, polyamides (e.g., nylon), polyesters, and fluorethylenes, for example.

U.S. Pat. No. 5,314,486 to Zang et al. discloses a phalangeal implant having an insertable bearing-surface. The implant lacks an ability to adjust alignment between respective joint components.

There is a need in the prior art for a simple but effective modular radial head prosthesis with fixation elements supporting articulating surfaces with improved properties and materials.

SUMMARY OF THE INVENTION

The invention provides a modular endoprosthetic radial head replacement implant. The implant features an end cap that fits into a cannulated body connected to an anchoring screw. The screw has a spherical head and fits into the cannulated body to engage complementary internal geometry of the cannulated body. The end cap is manufactured from a material that provides an appropriate bearing surface.

The invention is described herein mostly in connection with replacing the proximal end of a radius for articulating with the capitellum of a humerus. Other configurations are possible, however. The radial depression of the bearing surface can be radiused according to the type of joint being replaced, i.e., the depression can feature a single radius, a dual radius, an eccentric radius, etc. Also, the bases of the end cap and the base can be configured with a slant, for example, to sit flush with a variety of bone surfaces.

In an exemplary surgical technique for radial repair, an appropriated combination of modular components is selected to match a patient's anatomy. The fractured radius is resected using instrumentation configured to accommodate the implant. The threaded end of the screw is passed into the body to nest with the internal geometry of the body. The screw, engaged with a driver, is advanced with turning into the intermedullary canal of the radius. A spanner-type wrench may be used to rotate the body to improve fit or alignment. A jam nut is advanced along threads formed within the body and tightened onto the screw head. Once the screw is locked in place to maintain alignment with respect to the body, the end cap is assembled onto the body to complete the construct.

Other features and advantages of the present invention will become apparent from the following description of exemplary embodiments of the invention with reference to the accompanying drawings.

DETAILED DESCRIPTION OF THE INVENTION

Referring to FIGS. 1-4, an endoprosthetic radial head prosthesic implant 1 according to the present invention is shown. Implant 1 includes three component modules: an end cap 3, a body 5, and a screw 7. The components can be offered in a variety of interchangeable sizes and configurations, exemplary examples of which are described in further detail below.

End cap 3 may be manufactured from hydrogel, polished titanium, polished CoCr, PEEK, plastics and other polymers, and other biocompatible materials. Metal surfaces may be coated or treated to enhance bearing properties. Hydrogels are colloidal gels in which water is the dispersion medium. An exemplary hydrogel material contains water in similar proportions to human tissue, to which it has similar mechanical and physical properties. The hydrogel is an organic polymer-based biomaterial known to be highly biocompatible. Used in articular applications, the hydrogel material is soft and compliant like human tissue, and is exceptionally wear resistant and strong, making it an exemplary implant resource suitable for many medical applications.

Figure 7:
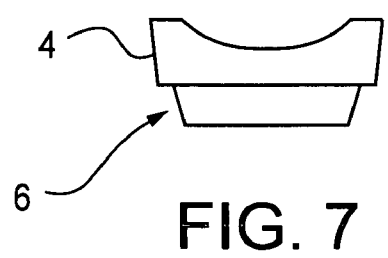
FIG. 7 is a side view of an alternative ceramic end cap formed with a Morse taper.

End cap 3 mates with the body 5. Joining of the two components may be accomplished by a "snap" fit in the case of non-metallic components. Metallic or ceramic end cap components 4 may be joined using a Morse type taper 6, as shown in FIG. 7, to a body 5 formed with complementary geometry.

The interface between the end cap 3 and body 5 may or may not contain index notches to allow for precise incremental radial adjustment. The base 8 of the end cap 3 may be slanted to provide better anatomical matching of the device to the anatomy, as illustrated by broken line 9 in FIG. 2.

Figure 1:
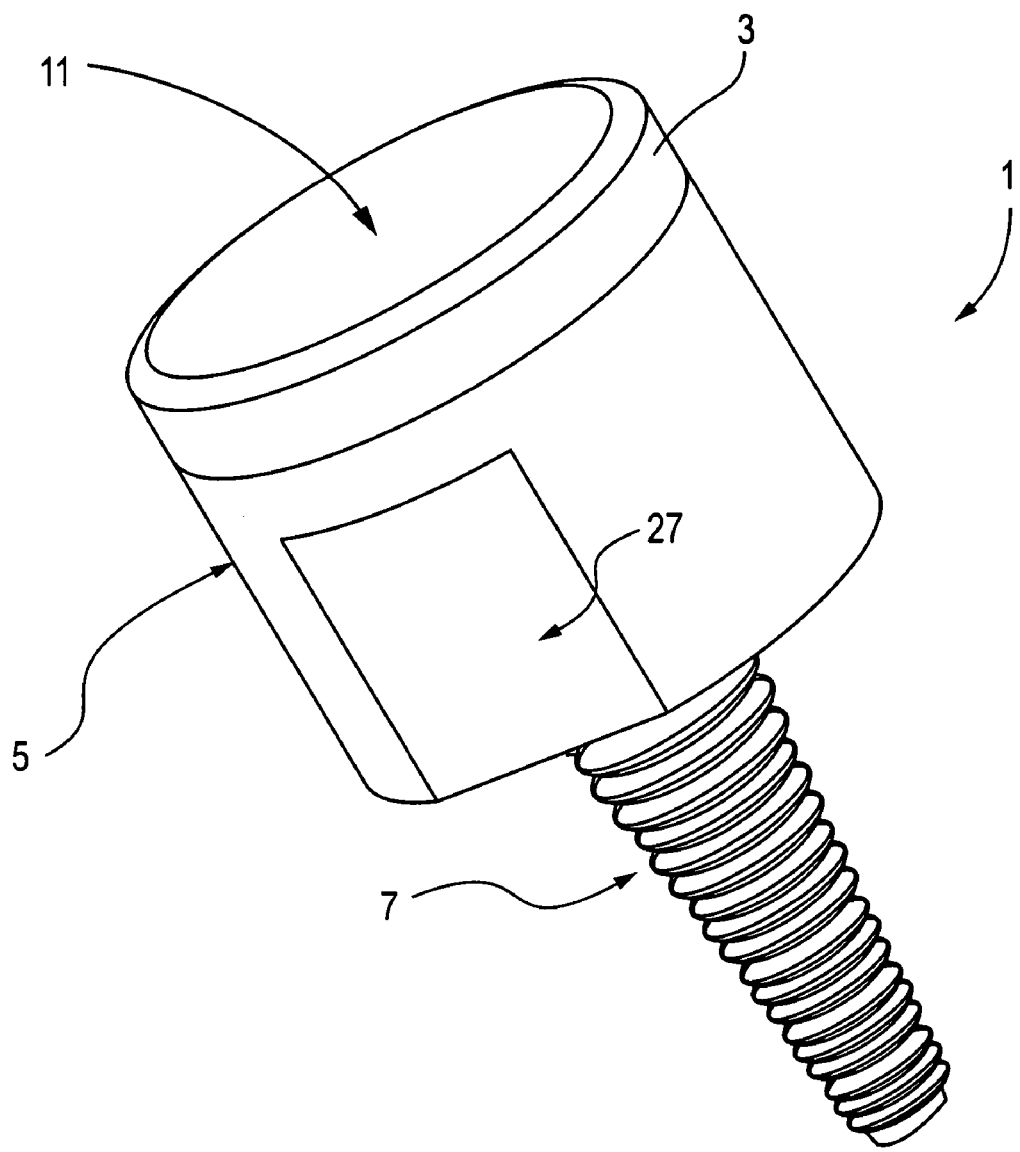
FIG. 1 is a perspective illustration of a modular radial head prosthesis with a single-radius end cap surface according to the present invention.
Figure 2:
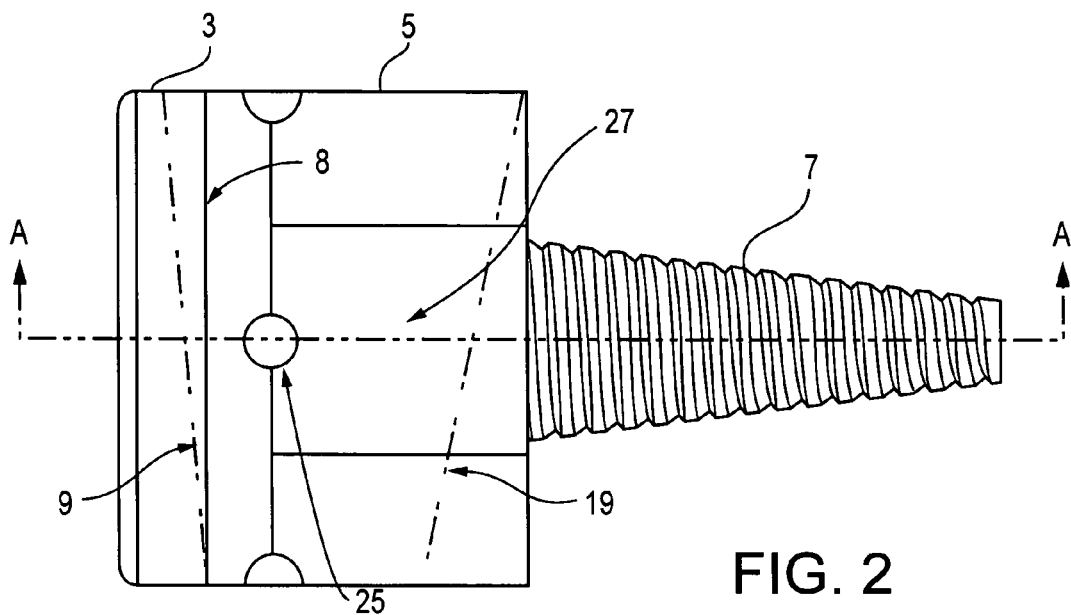
FIG. 2 is a plan view of the modular implant of FIG. 1, with alternative configurations shown by broken lines.
Figure 3:
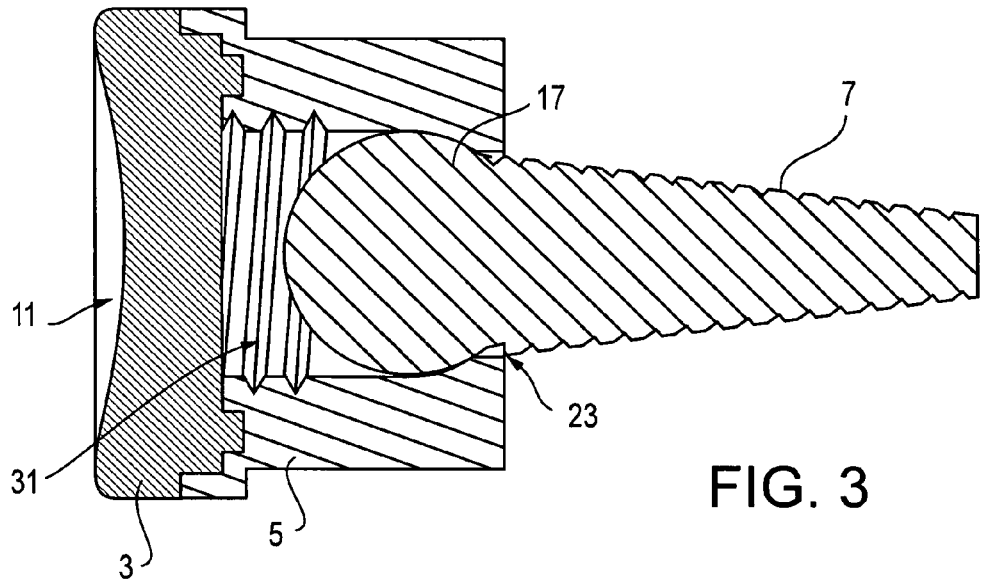
FIG. 3 is a cross-sectional view taken along the line A-A in FIG. 2.
Figure 4:
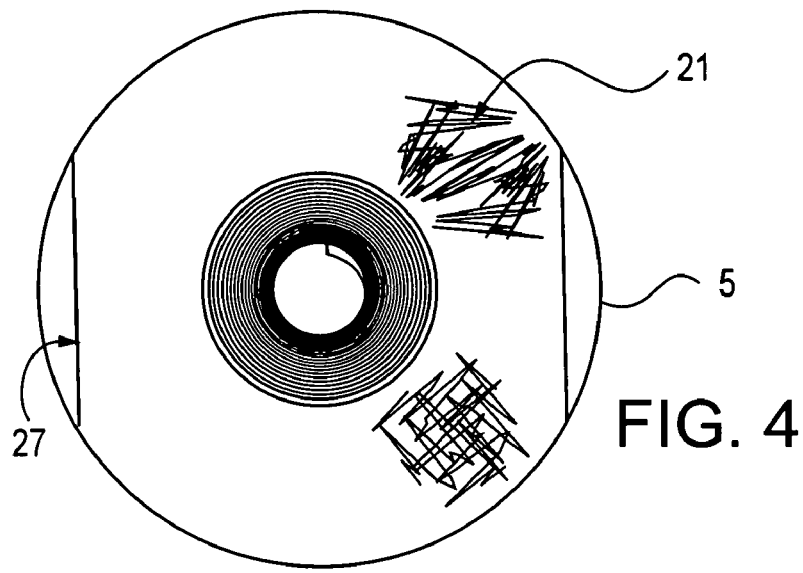
FIG. 4 is a view of the modular implant taken from the distal end of the screw to show the bone-engaging surface of the implant body.
Figures 5, 6:
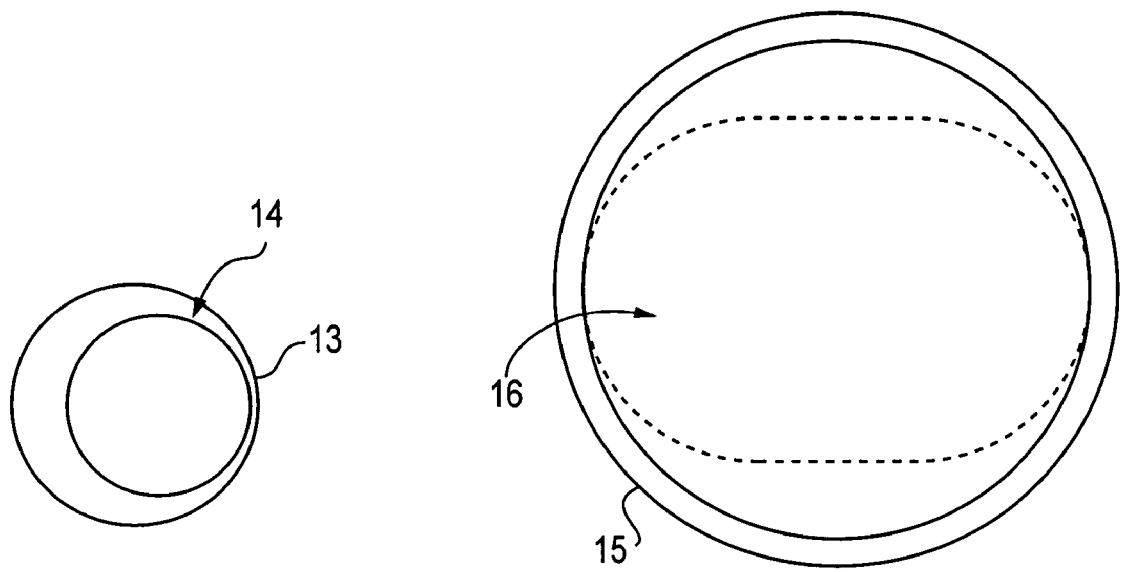
FIG. 5 is a view of the end cap proximal surface showing an alternative eccentric radius surface depression.
FIG. 6 is an enlarged view of the end cap proximal surface showing an alternative dual-radius surface depression.

External edges of the end cap 3 are substantially rounded. The central portion 11 is substantially concave and has a single radius. Referring to FIGS. 5 and 6, alternate configurations can incorporate an end cap 13 having a single radius eccentric concavity 14, or an end cap 15 having a dual radius concavity 16 to replicate possible translational motion found anatomically.

The cannulated body 5 can be manufactured from titanium alloy, or other biocompatible metallic or non-metallic materials. Body 5 assembles with the end cap 3 as described above to cover the proximal end of the body 5 cannulation. Once in place, the end cap 3 will enclose within body 5 a jam nut (not shown) and a screwhead 17, described in further detail below. Body 5 is substantially cylindrical, and may have a slanted distal end 19, shown by a broken line in FIG. 2, to provide better anatomical matching of base 5 to patient anatomy. The surface 21 of the distal end of base 5, shown in FIG. 4, may be modified by a single treatment or a combination of treatments to enhance fixation of the body 5, and hence the implant 1, to bone. These may include such improvements as bead blasting, porous coating, sintered metallic beads, hydroxyapatite, or other machined and/or biologic treatments not described.

Body 5 is formed to provide a hole 23 through the bottom surface 21. Internal geometry of body 5 adjacent the hole 23 is spherical to accommodate the head 17 of the screw 7. The complementary geometry of both components, body 5 and screw 7, provides improved contact surface area for locking the implant construct, as described further below. Additionally, the complementary configuration allows for polyaxial motion of the body 5 to place surface 21 in apposition to the resected radial bone, regardless of the angle of resection. The polyaxial adjustment is infinite within the mechanical constraints of the device.

A plurality of sockets 25 located radially about the central axis of body 5, on the major diameter, provides a method of attachment for a corresponding instrument. The instrument may be used to rotate the body 5 about it's central axis to position the body 5 for maximum implant 1 performance. Alternately, or in addition, other features or forms located radially, such as flats 27, may be employed to facilitate in situ rotation of the body 5.

Screw 7 may be manufactured from titanium alloy, or other metallic materials. The screw 7 preferably is manufactured from materials similar to those of the jam nut and body 5.

The screw 7 may be tapered or straight in design. The spherical head 17 is located proximally. The shape of the head 17 is complementary to the spherical radius found within the body 5. The head 17 of the screw 7 is formed to accept a corresponding tool to drive the implant forward with turning into bone.

Once polyaxial adjustment of the body 5 with respect to screw 7 is completed, as described above, the body 5 and screw 7 are locked into position. More specifically, the jam nut is assembled within the body 5. The externally-threaded jam nut is installed into complementary internally-threaded portion 31 of body 5. The jam nut is tightened onto spherical head 17 using a common tool. The adjusted polyaxial position can be unlocked as necessary by loosening the jam nut. The distal face of the jam nut is spherical to provide improved contact surface area with the spherical head 17 for locking the body 5/screw 7 construct.

The jam nut may be manufactured from titanium alloy or other metallic materials. The jam nut preferably is manufactured from materials similar to those of the screw 7 and body 5.

Preparation for an exemplary surgical technique relies upon radiographic film, surgical templates, and trial implants to determine and select the appropriate combination of modular devices end cap 3, body 5, screw 7 that make up implant 1 to meet the patient's anatomical requirements. The remaining fractured radius is resected using appropriate instrumentation designed specifically for the implant system.

The distal end of the screw 7 is passed through the proximal opening of the body 5 until the screw 7 is nestled within the complementary internal sphericity of the body 5. The screw 7 is located and advanced down the intermedullary canal of the radius until the distal surface 21 of body 5 is in apposition with the resected bone. A spanner type wrench may be used to rotate body 5 radially for improved fit or alignment. The jam nut is advanced and tightened to lock the screw 7 into place. The end cap 3 is assembled onto the body 5 to complete the construct.

Although the present invention has been described in connection with preferred embodiments, many modifications and variations will become apparent to those skilled in the art. It is not intended that the invention be strictly limited to the above-described and illustrated embodiments. Any modifications, including those presently unforeseeable, of the invention that come within the spirit and scope of the following claims should be considered part of the invention.

What is claimed is:

1. A modular endoprosthetic joint implant comprising:
a fixation element having a distal portion and a proximal portion, wherein the proximal portion includes a spherical head, and wherein the distal portion includes a threaded screw for insertion into a bone canal of a resected bone;
a cannulated body secured to the proximal portion of the fixation element and having a hole formed through a distal surface of the cannulated body, a portion of the body adjacent the hole having a spherical internal geometry complementary to the spherical head of the fixation element to allow polyaxial adjustment of the cannulated body such that the distal surface of the body is placed in apposition to the resected bone regardless of the angle of bone resection; and
an articular surface element disposed on a proximal surface of the cannulated body.

2. An endoprosthetic joint implant as in claim 1, wherein the articular surface element is contoured to engage a complementary articular surface.

3. An endoprosthetic joint implant as in claim 2, wherein the articular surface element has a concave contour with one of a single radius, a double radius, and an eccentric radius.

4. An endoprosthetic joint implant as in claim 1, wherein the articular element consists of hydrogel.

5. An endoprosthetic joint implant as in claim 1, wherein the articular element comprises at least one of a metal, a ceramic, and a plastic.

6. An endoprosthetic joint implant as in claim 1, further comprising a locking mechanism for locking a relative position between the cannulated body and the fixation element.

7. An endoprosthetic implant as in claim 1, wherein the distal surface is slanted.

8. An endoprosthetic implant as in claim 1, wherein the bottom surface is at least one of mechanically and biologically treated to enhance interactions between the implant and bone.

9. An endoprosthetic implant as in claim 1, wherein the cannulated body includes external features for engagement by a tool.

10. A method of joint surgery comprising:

resecting a bone to remove an articular head; and installing in place of the articular head a modular endoprosthetic joint implant comprising:

a fixation module having a distal portion and a proximal portion, the proximal portion including a spherical head; a cannulated body secured to the fixation module and having an internally-threaded portion, a distal surface and a proximal surface; and an articular surface element disposed on the proximal surface of the cannulated body, wherein the step of installing comprises: inserting the fixation module distally into the cannulated body and advancing the fixation module distally into an intermedullary canal; polyaxially adjusting the cannulated body to the fixation module; and placing the distal surface of the cannulated body in apposition to the resected bone regardless of the angle of bone resection.

11. A method of joint surgery as in claim 10, further comprising locking polyaxial alignment between the fixation module and the cannulated body.

12. A method of joint surgery as in claim 11, further comprising fitting the articular surface element onto a proximal end of the cannulated body to cover the cannulation.

* * * * *